United States Patent

Drauz et al.

Patent Number: 5,534,541
Date of Patent: Jul. 9, 1996

[54] COMPOUNDS FOR COMBATING PLANT DISEASE

[75] Inventors: Karlheinz Drauz, Freigericht; Jürgen Martens, Oldenburg, both of Germany

[73] Assignee: Degussa Aktiengesellschaft, Frankfurt am Main, Germany

[21] Appl. No.: 376,666

[22] Filed: Jan. 23, 1995

Related U.S. Application Data

[63] Continuation of Ser. No. 120,321, Sep. 14, 1993, abandoned, which is a continuation of Ser. No. 953,292, Sep. 30, 1992, abandoned, which is a continuation of Ser. No. 677,350, Mar. 29, 1991, abandoned.

[30] Foreign Application Priority Data

Apr. 6, 1990 [DE] Germany .................. 40 11 172.5

[51] Int. Cl.⁶ ........................... A01N 43/10; A01N 43/40
[52] U.S. Cl. ........................... 514/448; 514/423
[58] Field of Search ........................... 514/423, 448

[56] References Cited

U.S. PATENT DOCUMENTS 3,741,984 6/1973 Sheeran .
4,497,964 2/1985 Ojima et al. ........................... 549/72

*Primary Examiner*—Alan Siegel
*Attorney, Agent, or Firm*—Cushman Darby & Cushman

[57] ABSTRACT

Halogen thiophene carboxylic acid derivatives of the General Formula

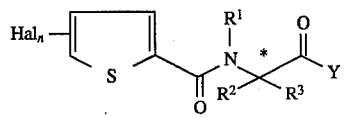

I in which Hal signifies chlorine or bromine, n the number 2 or 3, * signifies either an enantiomer or a racemate in the case of different $R^2$ and $R^3$ groups, $R^1$ stands for hydrogen or an alkyl group, $R^2$ stands for hydrogen, an alkyl group which can optionally be substituted by hydroxy-, carboxy-, alkoxy- or alkoxycarbonyl, mercapto- or alkylmercapto- or benzylmercapto, for an aryl group or aralkyl group, wherein the ring system can optionally be substituted with fluorine, chlorine or bromine atoms, for a cycloalkyl group or a cycloalkyl-methyl group, $R^3$ stands for hydrogen, an alkyl group, an alkenyl or alkynyl group or, optionally, $R^1$ and $R^3$ or $R^2$ and $R^3$ together can form an alkylene bridge in which one $CH^2$ unit can optionally be substituted by $NR^1$, O or S, Y signifies OH, $OR^4$ or $NR^5R^6$,
in which $R^4$ stands for an alkyl group whose H atoms are optionally replaced entirely or partially by halogen atoms, $R^5$ signifies hydrogen, an alkyl group, hydroxy- or an alkoxy group, $R^6$ signifies hydrogen, an alkyl group, a phenyl group or a cycloalkyl group or, optionally, $R^5$ and $R^6$ can form a ring with inclusion of the nitrogen atom and, optionally, of a further heteroatom. In addition, a method of their production is described. Compounds of General Formula I can be used in the form of plant protection products with suitable carrier materials.

5 Claims, No Drawings

COMPOUNDS FOR COMBATING PLANT DISEASE

This is a continuation of application Ser. No. 08/120,321, filed on Sep. 14, 1993, now abandoned, which was an FWC rule 62 of 07/953,292 filed Sep. 30, 1992, now abandoned, which was an FWC rule 62 of 07/677,350 filed Mar. 29, 1991, now abandoned.

The present invention relates to novel substances for combatting plant diseases. The invention also relates to the production of these substances as well as compositions containing at least one of these compounds as active ingredient. In addition, the invention relates to the use of these active ingredients or compositions containing them for the protection of plants against attack by harmful microorganisms, e.g. *phytotoxic fungi*, bacteria and viruses.

SUMMARY OF THE INVENTION

The subject matter of the invention is constituted by compounds of the General Formula I

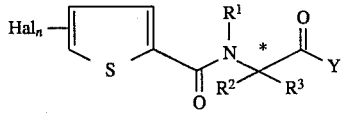

in which Hal signifies chlorine or bromine, n the number 2 or 3, * signifies either an enantiomer or a racemate in the case of different $R^2$ and $R^3$ groups, $R^1$ stands for hydrogen, a straight-chain or branched alkyl group with 1–4 carbon atoms, $R^2$ stands for hydrogen, a straight-chain alkyl group with 1–16 carbon atoms or for a branched-chain alkyl group with 3–16 carbon atoms which can optionally be substituted by hydroxy-, carboxy-, $C_1$–$C_6$ alkoxy- or $C_1$–$C_6$ alkoxycarbonyl, mercapto- or $C_1$–$C_6$ alkylmercapto- or benzylmercapto, for an aryl group with 6–10 carbon atoms or aralkyl group with 7–16 carbon atoms, wherein the ring system can optionally be substituted with 1–3 fluorine, chlorine or bromine atoms, for a cycloalkyl group with 3–8 carbon atoms, a cycloalkyl-methyl group with a total of 4–9 carbon atoms, $R^3$ stands for hydrogen, an alkyl group with 1–4 carbon atoms, an alkenyl or alkynyl group with 2–4 carbon atoms or, optionally, $R^1$ and $R^3$ or $R^2$ and $R^3$ together can form an alkylene bridge with 2–8 carbon atoms in which one $CH_2$ unit can be replaced by $NR_1$, O or S, Y signifies OH, $OR^4$ or

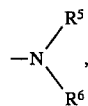

in which $R^4$ stands for an alkyl group with 1–4 carbon atoms whose hydrogen atoms are optionally replaced entirely or partially by halogen atoms, $R^5$ signifies hydrogen, an alkyl group with 1–6 carbon atoms, hydroxy- or an alkoxy group with 1–6 carbon atoms, $R^6$ signifies hydrogen, an alkyl group with 1–6 carbon atoms, or $R^6$ signifies a phenyl group or a cycloalkyl group with 3–8 carbon atoms or, optionally, $R^5$ and $R^6$ can form a 4–8 membered ring with inclusion of the nitrogen atom and optionally of a further heteroatom.

A preferred embodiment of the invention comprises compounds of Formula I which are characterized in that $R^1$ signifies hydrogen or an alkyl group with 1–3 carbon atoms, $R^2$ represents hydrogen, an alkyl group with 1–6 carbon atoms which can be unsubstituted or substituted by an alkoxycarbonyl group with 1–6 carbon atoms or $R^2$ is a phenyl-, aralkyl with 7 or 8 carbon atoms or cycloalkyl group with 3–7 carbon atoms, $R^3$ is hydrogen or alkyl group with 1–4 carbon atoms or $R^2$ and $R^3$ together form an alkylene bridge with 2 carbon atoms and Y is OH, $OR^4$ or $NR^5R^6$ in which $R^4$ signifies an alkyl group with 1–4 carbon atoms whose hydrogen atoms can be entirely or partially replaced by fluorine and $R^5$ and $R^6$ signify, independently of one another, hydrogen or alkyl with 1–4 carbon atoms or alkoxy with 1–4 carbon atoms or in which $R^5$ and $R^6$ form a 5–6 membered ring together with the N atom which ring does not contain or contains one further N or O.

A further preferred embodiment of the invention comprises compounds of Formula I which are characterized in that Hal signifies bromine, n the number 2 and $R^1$ hydrogen.

A further preferred embodiment of the invention comprises compounds of Formula I in which $R^2$ signifies hydrogen or an alkyl group with 1–4 carbon atoms which can be unsubstituted or substituted by an alkoxy carbonyl group with 1–2 carbon atoms, $R^3$ is hydrogen, methyl or ethyl and Y signifies OH, $OR^4$ or $NR^5R^6$, in which $R^4$ signifies an alkyl group with 1–4 carbon atoms and $R^5$ and $R^6$ signify, independently of one another, hydrogen or an alkyl group with 1–4 carbon atoms.

A further preferred embodiment of the invention comprises compounds of Formula I which are characterized in that $Hal_n$ signifies 2 bromine atoms in positions 2' and 3' of the thiophene ring.

The invention also provides a method for the production of compounds of the General Formula I which is characterized in that an acid halide of the General Formula II

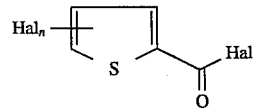

Hal=Cl, Br
n=2 or 3
is reacted with an amino component of General Formula III

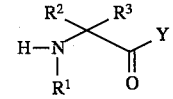

in which $R^1$, $R^2$, $R^3$ and Y have the meanings discussed above.

The invention also provides compositions for combatting phytopathogenic germs and for preventing the attack of disease in plants which contain, as active ingredient, at least one compound of General Formula I together with auxiliary agents which are conventional in the formulation of horticultural and agricultural compositions.

The invention also provides a method for the production of compositions for combatting phytopathogenic germs and for preventing the attack of diseases in plants which contain, as active ingredient, at least one compound according to General Formula I in combination with auxiliary agents which are conventional in the formulation of horticultural and agricultural compositions.

It was further found that compounds of General Formula I can be used to combat phytopathogenic bacteria and to prevent the attack of disease in plants.

Finally, a method has been found in which plants are protected from attack by disease by means of the treatment of the plants, or parts of them or of their growing site with an effective amount of a compound of General Formula I.

The compounds of General Formula II can be produced according to known methods, starting with carboxylic acids IV, which can also be obtained by methods known in the literature[1-12].

1. D. Pillon et al. Chimie Therapeutique 1, 1970, 32
2. DOS 1 813 195
3. French patent application 1,563,735
4. U.S. Pat. No. 3,887,354
5. U.S. Pat. No. 3,536,473
6. U.S. Pat. No. 3,303,210
7. J.A. 7,014,560-R
8. EP 216,279
9. Ber. Dtsch. Chem. Ges. [Berichte der Deutschen Chemischen Gesellschaft] 18, 2308 (1885)
10. Liebigs. Ann. Chem. 532, 250 (1937)
11. ibid. 511/512 p. 136, 1934.
12. J. Indian Chem. Soc. 59, 283 (1982)

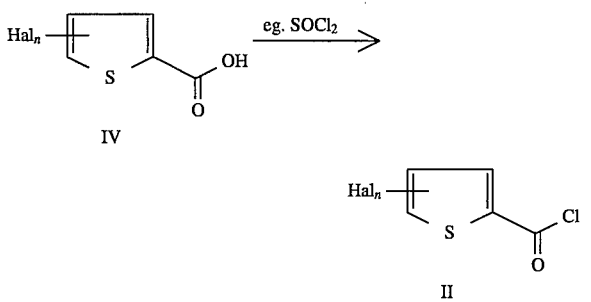

In particular, 2,3-dibromothiophene-5-carboxylic acid bromide can be obtained directly and in a good yield by means of the reaction of thiophene-2-carboxylic acid with thionyl chloride, reaction of the thiophene-2-carbonyl chloride obtained with elementary bromine at 90°–100° C., isolation of the acid bromide and subsequent fractional distillation in a high vacuum.

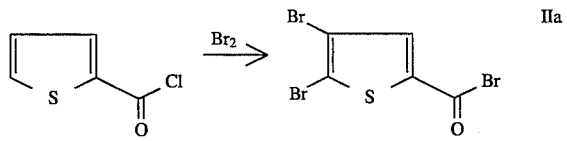

The compounds of General Formula III are produced from the corresponding optically active or racemic amino acids.

The amino acid esters III ($Y=OR^4$) are likewise produced according to methods known in the literature (Houben-Weyl, volume 15/1, pp. 315–338; Georg Thieme Verlag, Stuttgart 1974; parallel German Patent Application (P 40 11 171.7). The amino acid amides III ($Y=NR^5R^6$) can be obtained by means of a) The reaction of N-protected α-amino acid methyl esters with ammonia or amines, especially alkyl amines or by means of the reaction of active esters of N-protected α-amino acids such as e.g. p-nitrophenyl esters or mixed anhydrides which can be produced from N-protected α-amino acid salts of the alkali metals and acid chlorides or chloroformic acid esters with the corresponding amino components and a subsequent splitting off of the N protective groups (cf. Houben-Weyl, volume 15/1, pp. 453–457, Georg Thieme Verlag, Stuttgart 1974) or b) by reacting N-carboxy anhydrides, the production of which is described e.g. in H. R. Kricheldorf, α-Aminoacid-N-Carboxy-Anhydrides and Related Heterocycles, Springer-Verlag, Berlin, Heidelberg, 1987, pp. 3–51 with less reactive amines (ibid., pp. 59–71).

The reaction of the acid halides of General Formula II with the amines of General Formula III preferably takes place in water or organic solvents such as e.g. carboxylic acid esters, halogenated hydrocarbons, ethers or mixtures thereof; NaOH, KOH, carbonates and hydrogen carbonates as well as tert. amines and pyridine are preferably used as bases. These bases can function at the same time as solvent (Example 35). The temperature of the reaction is not critical; depending on the reactivity of the component, a temperature range between –10° C. and the boiling point of the particular solvent or solvent mixture is to be selected. The reactions are carried out with advantage at 5° C.–25° C.

The reaction components and the bases are preferably reacted in stoichiometric amounts. The following procedure is used: The acid halide of General Formula II in the particular solvent is added to a suspension or solution of the amino compounds of General Formula III and of the base in the solvent. After the reaction has taken place, amine hydrochloride is filtered off, to the extent that the work is performed in purely organic systems, the solvent distilled off, the residue washed with water and optionally crystallized with a further solvent. When working in water or aqueous mixtures, either the solid product is filtered and subsequently washed with water or the oils obtained are extracted with a solvent immiscible with water, this solvent washed neutral with water, dried and distilled off. Solid residues likewise remain which exhibit sufficient purity directly or after washing or recrystallization. The products obtained are then dried at temperatures between 20°–50° C. until the weight is constant.

It was surprisingly found that the compounds of General Formula I of the invention prevent plants from being attacked by harmful microorganisms when they are used and thus prevent damage to the plant caused by the attack.

It is characteristic of the active ingredients of the invention that the protection of plants can occur both by means of a direct effect on the plant-damaging microorganisms by means of leaf applications (direct action) or by means of soil applications (systemic action). On account of the very good mode of action of the compounds of General Formula I of the invention, a broad spectrum of protection of plants against diseases can be achieved. The use of the active ingredients of the invention is therefore especially suited for practical conditions. In addition, the systemic activity of the compounds of General Formula provides a protective effect which also extends to growing plant parts of the plant treated.

The general plant-protecting activity of the active ingredients of the invention is effective e.g. against the following classes of phytopathogenic fungi: *Fungi imperfecti* (e.g. *Botrytis, Helminthosporium, Fusarium, Septoria, Cercospora* and *Alternaria*); *Basidiomycetes* (e.g. the genera *Hemileia, Rhizoctonia, Puccinia*); *Ascomycetes* (e.g. *Venturia, Podosphaera, Erysiphe, Monilia, Uncinula*).

In addition, the active ingredients can be used in an especially advantageous manner against the following harmful organisms: Fungi such as e.g. *Oomycetes* (e.g. *Plasmopara viticola, Phytophthora infestans, Peronospora tabacina, Pseudoperonospora*), *Fungi imperfecti* (e.g. *Colletotrichum lagenarium, Pyricularia oryzae, Cercospora*

*nicotinae*), *Ascomycetes* (e.g. *Venturia inaequalis*): bacteria such as e.g. *Pseudomonads* (*Pseudomonas lachrymans, Pseudomonas tomato, Pseudomonas tabaci*); *Xanthomonads* (e.g. *Xanthomonas oryzae, Xanthomonas vesicatoria*); *Erwinia* (e.g. *Erwinia amylovora*); and viruses such as e.g. the tobacco mosaic virus.

The compounds of the invention can be used for protecting plants of various useful crops.

The following plant types, for example, are suitable for the use of the compounds of the invention: grains (wheat, barley, rye, oats, rice, sorghum and related gains); beets (sugar beets and fodder beets); pomaceous fruit, stone fruit and berries (apples, pears, plums, peaches, almonds, cherries, strawberries, raspberries and blackberries); legumes (beans, lentils, peas, soy beans); oil crops (rape, mustard, opium poppy, olives, sunflowers, coconut, castor oil plant, cocoa, peanuts); the gourd family (pumpkin, cucumbers, melons); fiber plants (cotton, flax, hemp, jute); citrus fruits (oranges, lemons, grapefruit, tangerines); various vegetables (spinach, head lettuce, asparagus, various types of cabbage, carrots, onions, tomatoes, potatoes, pepper);

Laurel plants (avocado, cinnamon, camphor) or plants such as corn, tobacco, nuts, coffee, sugarcane, tea, wine grape vines, hops, banana plants and natural rubber plants as well as ornamental plants (flowers, bushes, leafy trees and needle trees such as conifers). This enumeration is not intended to limit the invention, but to illustrate the wide variety of plants which can be treated.

The following plants are especially suitable for the application of the method of the invention: Cucumber, tobacco, vines, rice, pear, pepper, potatoes, tomato and apple.

The compounds of General Formula I are used in unchanged form or preferably together with the auxiliary agents which are conventional in the formulation art and are therefore processed in a known manner e.g. to emulsion concentrates, directly sprayable or dilutable solutions, dilute emulsions, wettable powders, soluble powders, dusting agents, granulates or also encapsulations in, e.g., polymeric substances. The methods of use such as spraying, misting, dusting, spreading or pouring are selected as are the type of carrier in accordance with the desired effect and the conditions.

The formulations, that is, the agents, preparations or compositions containing the active ingredient of General Formula I and, optionally, a solid or liquid additive are produced in a known manner, e.g. by means of an intimate mixing and/or grinding of the active ingredients with extenders such as solvents, solid carrier substances and, optionally, surface-active compounds (tensides).

Potential solvents are: Aromatic hydrocarbons, preferably the fractions $C_8$ and $C_{12}$ such as e.g. xylene mixtures or substituted naphthalenes, phthalic acid esters such as dibutyl or dioctylphthalate, aliphatic hydrocarbons such as cyclohexane or paraffins, alcohols and glycols as well as their ethers and esters such as ethanol, ethylene glycol, ethylene glycol monomethyl or ethyl ether, ketones such as cyclohexanone, strongly polar solvents such as N-methyl-2-pyrrolidone, dimethyl sulfoxide or dimethyl formamide as well as optionally epoxidized vegetable oils such as epoxidized coconut oil or soy-bean oil or water.

As a rule, natural ground stone such as calcite, talcum, kaoline, montmorillonite or attapulgite are used as solid carrier substances, e.g., for dusting agents and dispersible powders. In order to improve the physical properties, highly disperse silica or highly disperse, absorbent polymerizates can be added. Potential granular, adsorptive granulate carriers are porous types such as pumice, broken bricks, sepiolite or bentonite, potential nonsorptive carrier materials are e.g. calcite or sand. In addition, a great number of pregranulated materials of an inorganic or organic nature, especially dolomite or comminuted plant residues, can be used.

Potential surface-active compounds are, depending on the type of the active ingredient of General Formula I to be formulated, non-ionic, cationic and/or anionic surface active agents having good emulsifying, dispersing and wetting properties. Surfactant mixtures are also to be understood under the term surfactants.

Suitable anionic surfactants can be both so-called water-soluble soaps and water-soluble synthetic surface-active compounds.

Suitable soaps are the alkali salts, alkaline-earth salts or optionally substituted ammonium salts of higher fatty acids ($C_{10}$–$C_{22}$) such as the Na or K salts of oleic or stearic acid, or of natural fatty-acid mixtures which can be obtained e.g. from coconut oil or tallow oil. Moreover, the fatty-acid methyl taurine salts are also suitable.

However, so-called synthetic surfactants are more frequently used, especially fatty sulfonates, fatty sulfates, sulfonated benzimidazole derivatives or alkylaryl sulfates.

The fatty sulfonates or fatty sulfates are generally present as alkali salts, alkaline-earth salts or optionally substituted ammonium salts and comprise an alkyl group with 8 to 22 carbon atoms; alkyl also includes the alkyl part of acyl groups, e.g. the Na or Ca salt of of lignosulfonic acid, of dodecylsulfuric acid ester or of a fatty alcohol sulfate mixture prepared from natural fatty acids. The salts of sulfuric acid esters and sulfonic acid from fatty alcohol ethylene oxide adducts also are useful. The sulfonated benzimidazole derivatives preferably contain 2 sulfonic acid groups and one fatty acid group with 8 to 22 carbon atoms. Alkylarylsulfonates are e.g. the Na, Ca or triethanol amine salts of dodecylbenzene sulfonic acid, of dibutylnaphthaline sulfonic acid or of a naphthalene sulfonic acid formaldehyde condensation product.

Other potential substances are corresponding phosphates, e.g. salts of phosphoric acid ester of a p-nonylphenol-(4-14)-ethylene oxide adduct and phospholipids.

Potential non-ionic surfactants are first of all polyglycol ether derivatives of aliphatic or cycloaliphatic alcohols, saturated or unsaturated fatty acids and alkyl phenols which can contain 3 to 30 glycol ether groups and 8 to 20 carbon atoms in the (aliphatic) hydrocarbon group and 6 to 8 carbon atoms in the alkyl group of the alkyl phenols.

Further suitable non-ionic surfactants are the water-soluble polyethylene oxide adducts of polypropylene glycol, which adducts contain 20 to 250 ethylene glycolether groups and 10 to 100 propylene glycol ether groups, ethylene diaminopropylene glycol and alkylpolypropylene glycol with 1 to 10 carbon atoms in the alkyl chain. The named compounds customarily contain 1 to 5 ethylene glycol units per propylene glycol unit.

Nonylphenol polyethoxyethanols, castor-oil polyglycolether, polypropylene-polyethylene oxide adducts, tributylphenoxypolyethanol, polyethylene glycol and octylphenoxypolyethoxyethanol are mentioned as examples of nonionic surfactants.

In addition, fatty-acid esters of polyoxyethylene sorbitan as well as polyoxyethylene sorbitan trioleate can also be considered.

The cationic surfactants are especially quaternary ammonium salts which comprise as N substituent at least one alkyl group with 8 to 22 carbon atoms and optionally halogenated alkyl, benzyl or low hydroxyalkyl groups as further substituents. The salts are preferably present as halides, methyl sulfates or ethyl sulfates, e.g. stearyltrimethyl ammonium chloride or benzyldi-(2-chloroethyl)-ethyl ammonium bromide.

The surfactants conventionally used in the formulation art are described in the following publications, among others: "Mc Cutcheon's Detergents and Emulsifiers Annual", MC Publishing Corp., Ridgewood, N.J., 1979; Dr. Helmut Stache "Tensid Taschenbuch", Carl Hanser Verlag, Munich/Vienna 1981.

The pesticide preparations generally contain 0.1 to 99% by weight, especially 0.1 to 95% by weight, active ingredient of General Formula I, 1 to 99.9% by weight of a solid or liquid additive and 0 to 25% by weight, especially 0.1 to 25% by weight, of a surfactant.

Whereas concentrated agents tend to be preferred as a commercial item, the enduser generally uses dilute agents.

The agents can also contain further additives such as stabilizers, defoamers, viscosity regulators, binders, adhesive agents as well as fertilizers or other active substances for the obtention of special effects.

EXAMPLES OF FORMULATION

Examples of Formulation for Liquid Active Ingredients of General Formula I

%=percent by weight

| Emulsion concentrates | a) | b) | c) |
|---|---|---|---|
| Active substance from the tables | 25% | 40% | 50% |
| Ca-docecylbenzene sulfonate | 5% | 8% | 6% |
| Castor oil polyethylene glycol ether (36 moles ethylene oxide) | 5% | — | — |
| Tributylphenoxy polyethylene glycol ether (30 moles ethylene oxide) | — | 12% | 4% |
| Cyclohexanone | — | 15% | 20% |
| Xylene mixture | 65% | 25% | 20% |

Emulsions of any desired concentration can be produced from such concentrates by diluting with water.

| Solutions | a) | b) | c) | d) |
|---|---|---|---|---|
| Active ingredient from the tables | 80% | 10% | 5% | 95% |
| Ethylene glycol monomethylether | 20% | — | — | — |
| Polyethylene glycol MG 400 | — | 70% | — | — |
| N-methyl-2-pyrrolidone | — | 20% | — | — |
| Epoxidized coconut oil | — | — | 1% | 5% |
| Petroleum ether (boiling limits 160–190° C.) (MG = molecular weight) | — | — | 94% | — |

The solutions are suitable for being used in the form of very small drops.

| Granulates | a) | b) |
|---|---|---|
| Active ingredient from the tables | 2% | 5% |
| Kaoline | 1% | 5% |
| Highly disperse silicic acid | 97% | — |
| Attapulgite | — | 90% |

The active ingredient is dissolved in methylene chloride, sprayed onto the carrier and the solvent subsequently evaporated in a vacuum.

| Dusting agent | a) | b) |
|---|---|---|
| Active ingredient from the tables | 2% | 5% |
| Highly disperse silicic acid | 1% | 5% |
| Talcum | 97% | — |
| Kaoline | — | 90% |

Ready-to-use dusting agents are obtained by intimately mixing the carrier substances with the active ingredient.

Formulation Examples for Solid Active Ingredients of General Formula I

%=Percent by Weight)

| Wettable powder | a) | b) | c) |
|---|---|---|---|
| Active ingredient from the tables | 25% | 40% | 50% |
| Na-lignosulfonate | 5% | 8% | 6% |
| Na-diisobutylnaphthaline sulfonate | | | |
| Na Lauryl Sulfate | — | — | — |
| Octylphenol polyethylene glycol ether (7–8 moles ethylene oxide) | — | — | — |
| Highly disperse silica | 65% | 25% | 20% |
| Kaoline | — | — | — |

The active ingredient is mixed with the additives and homogeneously ground in a suitable mill. Wettable powders are obtained which can be diluted with water to suspensions of any desired concentration.

| Emulsion concentrates | |
|---|---|
| Active ingredient from the tables | 10% |
| Octylphenol polyethylene glycol ether (4–5 moles ethylene oxide) | 3% |
| Ca-dodecylbenzene sulfonate | 3% |
| Castor oil polyglycol ether (35 moles ethylene oxide) | 4% |
| Cyclohexanone | 30% |
| Xylene mixture | 50% |

Emulsions of any desired concentration can be produced from this concentrate by diluting with water.

| Dusting agent | a) | b) |
|---|---|---|
| Active ingredient from the tables | 5% | 8% |
| Talcum | 95% | — |
| Kaoline | — | 92% |

The active ingredient is mixed with the carrier substances and ground in an appropriate mill.

| Extruder granulate | |
|---|---|
| Active ingredient from the tables | 10% |
| Na-lignosulfonate | 2% |
| Carboxymethylcellulose | 1% |
| Kaoline | 87% |

The active ingredient is mixed with the additives, ground and moistened with water. This mixture is extruded and then dried in a current of air.

| Encased granulate | |
|---|---|
| Active ingredient from the tables | 3% |
| Polyethylene glycol (MG 200) | 3% |
| Kaoline | 94% |

(MG = molecular weight)
The finely ground active ingredient is uniformly applied in a mixer onto the kaoline moistened with polyethylene glycol. This yields dust-free encased granulates.

| Suspension concentrate | |
|---|---|
| Active ingredient from the tables | 40% |
| Ethylene glycol | 10% |
| Nonylphenol polyethylene glycol ether (15 moles ethylene oxide) | 6% |
| N-lignosulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is intimately mixed with the additives. A suspension concentrate is obtained from which suspensions of any desired concentration can be produced by diluting with water.

EXAMPLE 1

670 g thiophene-2-carboxylic acid are mixed with 1243 g (760 ml) freshly distilled thionyl chloride under agitation and slowly heated. A clear solution is produced after 2.5 hours at 30° C. The mixture is then agitated 2 hours further under reflux. The excess thionyl chloride is then distilled off and 734 g (95.7% of theory) thiophene-2-carboxylic acid chloride are distilled over at 83° C./20 mbars.

605 g thiophene-2-carboxylic acid chloride are heated to 110° C. and 2077 g (668 ml) bromine are added drop-by-drop under agitation within 90 min, whereupon HBr gas escapes. The mixture is then agitated a further 148 hours at 100° C. After the end of the reaction, residual HBr and traces of bromine are removed by applying a gentle vacuum and the mixture is then fractionally distilled 1236 g of a fraction (85.8% of theory) are obtained at 94° C. and 0.2 mbars of 2,3 dibromothiophene-5-carboxylic acid bromide. Melting point 38°–40° C. The elementary analytic values correspond to the calculated values.

$^1$H-NMR (CDCl$_3$): 7.75 ppm (s, 1H)

8.0 g 2,3-dibromothiophene-5-carboxylic acid bromide dissolved in 50 ml THF (tetrahydrofuran) are added drop-by-drop to a suspension of 2.88 g glycine methyl ester•HCl and 4.62 g triethylamine in 100 ml THF at 20°–25° C. within 3 hours. The thick suspension produced is subsequently stirred another 2 hours at the same temperature, filtered and the filtrate concentrated by evaporation in a water-jet vacuum.

The residue obtained in this manner is thoroughly washed with 2×50 ml H$_2$O per time and washed after filtering with 100 ml petroleum ether and then dried at 40° C./30 mbars until weight constancy.

5.3 g (71.1% of theory) N-(2',3'-dibromo-5'-thenoyl)glycine methyl ester with a melting point of 97°–99° C. are obtained.

EXAMPLE 2

15 g 2,3-dibromothiophene-5-carboxylic acid bromide dissolved in 50 ml THF are added drop-by-drop to a solution of 6.6 g glycine isopropyl ester•HCl and of 8.7 g triethyl amine in 10 ml THF within 3 hours at 25° C. The mixture is then agitated 2 hours at 25° C., liquids are removed by suction from the precipitated solid matter, the filtrate is concentrated by evaporation and residual solvent is removed in a high vacuum, at which time crystallization occurs. The crystals are washed with n-pentane, filtered off and dried at 50° C./30 mbars to constant weight.

15.1 g (88.1% of theory) N-(2',3'-dibromo-5-thenoyl)glycine isopropyl ester with a melting point of 100°–102° C. are obtained.

EXAMPLE 3

A suspension of 1.87 g DL-alanine isopropyl ester•HCl and 2.25 g triethyl amine in 100 ml THF is reacted with a solution of 3.89 g 2.3-dibromothiophene-5-carboxylic acid bromide in 50 ml THF in the manner described in Example 1.

After workup, 3.26 g (73.3% of theory) N-(2',3'-dibromo-5'-thenoyl)-DL-alanine isopropyl ester with a melting point of 117°–118° C. are obtained.

EXAMPLE 4

A suspension of 2.20 g α-amino isobutyric acid methyl ester•HCl and 2.89 g triethyl amine in 100 ml diisopropyl ether is reacted with a solution of 5.0 g 2,3-dibromothiophene-5-carboxylic acid bromide in 50 ml diisopropyl ether.

After workup, 4.1 g (74.1% of theory) N-(2',3'-dibromo-5'-thenoyl)-2-amino isobutyric acid methyl ester with a melting point of 137°–138° C. are obtained.

EXAMPLE 5

A suspension of 3.1 g 1-amino cyclohexane carboxylic acid methyl ester•HCl and 3.99 g triethyl amine in 100 ml methyl-tert.-butyl ether (MTBE) is reacted with a solution of 6.0 g 2,3-dibromothiophene-5-carboxylic acid chloride by the method of Example 1.

After workup, 6.0 g (72% of theory) (2',3'-dibromo-5'-thenoyl)-1-amino cyclohexane carboxylic acid methyl ester with a melting point of 149°–150° C. are obtained.

EXAMPLE 6

A solution of 7.2 g L-valine methyl ester•HCl with 8.7 g triethyl amine in 100 ml THF is reacted by the method of Example 2 with a solution of 15 g 2,3-dibromothiophene-5-carboxylic acid bromide in 50 ml THF.

After workup, 15.1 g (88.1% of theory) N-(2',3'-dibromo-5'-thenoyl)-L-valine methyl ester with a melting point of 100°–102° C. are obtained.

EXAMPLE 7

7.2 g D-valine methyl ester•HCl, 8.7 g triethyl amine and 15 g 2,3-dibromothiophene-5-carboxylic acid bromide are reacted by the method of Example 6 in a total of 150 ml THF.

After workup, 14.9 g (86.8% of theory) N-(2',3'-dibromo-5'-thenoyl)-D-valine methyl ester with a melting point of 99°–101° C. are obtained.

EXAMPLE 8

A suspension of 2.36 g L-valine-2',2',2'-trifluoroethyl ester•HCl and 2.02 g triethyl amine in 100 ml THF is reacted by the method of Example 1 with a solution of 3.04 g 2,3-dibromothiophene-5-carboxylic acid in 50 ml THF.

After workup, 3.42 g (73.2% of theory) N-(2',3'-dibromo-5'-thenoyl)-L-valine-2 ",2",2"-trifluoroethyl ester with a boiling point of 52°–53° C. are obtained.

EXAMPLE 9

A suspension of 4.13 g L-valine-n-butyl ester•HCl and 4.0 g triethyl amine in 100 ml THF is reacted according to Example 1 with a solution of 6.0 g 2,3-dibromothiophene-5-carboxylic acid chloride in 50 ml THF.

After workup, 7.12 g (81.9% of theory) N-(2',3'-dibromo-5'-thenoyl)-L-valine-n-butyl ester is obtained as a viscous oil.

The reactions in Examples 10–30 are carried out in a manner analogous to Example 1 (See table 1).

TABLE 1
| Example | AS-Ester.HCl o.Amide.HCl [g] | 2.3-Dibromo-thiophen-5-carbonyl halide [g] | Base [g] | Solvent [ml] | Product Yield (gram)/Melting Point |
|---|---|---|---|---|---|
| 10 | 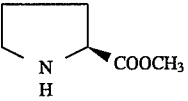 1.5 | -bromide 4.0 | NEt₃, 2.31 | THF, 150 | 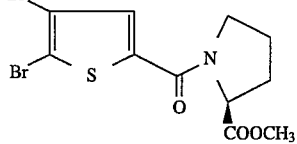 4.0/107–109° C. |
| 11 | 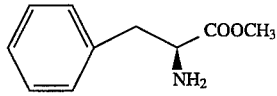 2.47 | -bromide 4.0 | NEt₃, 2.31 | THF, 150 | 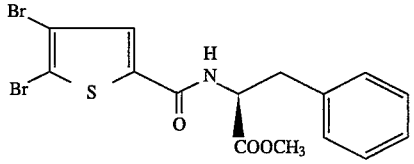 3.1/Viscous oil |
| 12 | 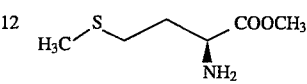 9.57 | -bromide 15.0 | NEt₃, 8.7 | THF, 150 | 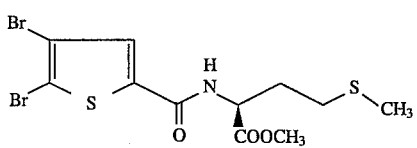 14.5/Viscous oil |
| 13 | 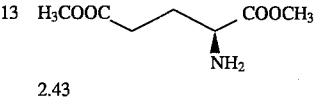 2.43 | -bromide 4.0 | NEt₃, 2.31 | THF, 150 | 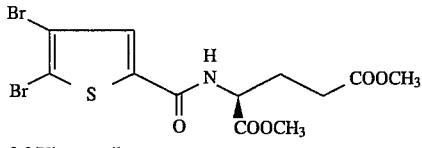 3.8/Viscous oil |
| 14 | 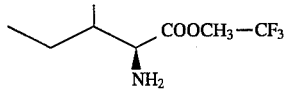 3.29 | -chloride 3.97 | NEt₃, 2.63 | THF, 150 | 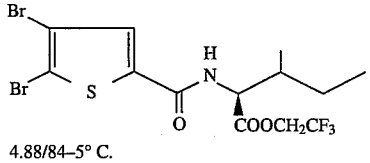 4.88/84–5° C. |
| 15 | 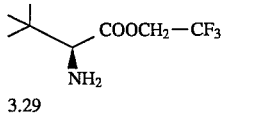 3.29 | -chloride 3.97 | NEt₃, 2.63 | THF, 150 | 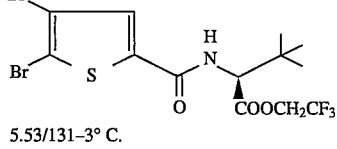 5.53/131–3° C. |
| 16 | 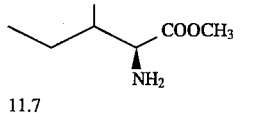 11.7 | -chloride 22.5 | NEt₃, 13.05 | THF, 150 | 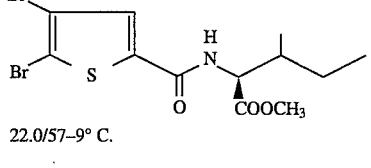 22.0/57–9° C. |
| 17 | 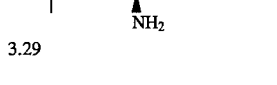 3.29 | -chloride 3.97 | NEt₃, 2.63 | THF, 150 | 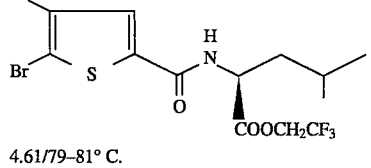 4.61/79–81° C. |

TABLE 1-continued

| Example | AS-Ester.HCl o.Amide.HCl [g] | 2,3-Dibromo-thiophen-5-carbonyl halide [g] | Base [g] | Solvent [ml] | Product Yield (gram)/Melting Point |
|---|---|---|---|---|---|
| 18 | (CH₃)₂CHCH₂-CH(NH₂)-COOCH₃ 7.81 | -bromide 15.0 | NEt₃, 8.7 | THF, 150 | 5-(4,5-dibromothiophene-2-carboxamido)-methyl 4-methylpentanoate derivative 16.1/100–02° C. |
| 19 | (CH₃)₃C-CH(NH₂)-COOCH₃ 7.81 | -bromide 15.0 | NEt₃, 8.7 | THF, 150 | tert-butyl-glycine methyl ester amide 14.7/125–128° C. |
| 20 | (CH₃)₂CH-CH(NH₂)-COOCH₂CF₃ 2.36 | -chloride 3.04 | NEt₃, 2.02 | THF, 150 | valine 2,2,2-trifluoroethyl ester amide 3.42/52–3° C. |
| 21 | (CH₃)₂CH-C(CH₃)(NH₂)-COOCH₃ 3.12 | -chloride 5.23 | NEt₃, 3.46 | THF, 100 | α-methylvaline methyl ester amide 5.8/107–109° C. |
| 22 | CH₃CH₂-CH(NH₂)-COOCH₃ 2.68 | -chloride 5.23 | NaHCO₃ 2.88 | H₂O, 100 THF, 50 | α-aminobutyric acid methyl ester amide 5.96/68–70° C. |
| 23 | CH₃CH₂CH₂-CH(NH₂)-COOCH₃ 2.88 | -chloride 5.23 | NEt₃ 3.48 | THF, 150 | norvaline methyl ester amide 6.09/79–81° C. |
| 24 | CH₃(CH₂)₃-CH(NH₂)-COOCH₃ 3.18 | -chloride 5.23 | NEt₃ 3.48 | THF, 150 | norleucine methyl ester amide 6.15/59–61° C. |
| 25 | H₃C-NH-CH₂-COOC₂H₅ 2.64 | -chloride 5.23 | NEt₃ 3.48 | THF, 150 | sarcosine ethyl ester amide 5.63/80–82° C. |

TABLE 1-continued

| Example | AS-Ester.HCl o.Amide.HCl [g] | 2.3-Dibromthiophen-5-carbonyl halide [g] | Base [g] | Solvent [ml] | Product Yield (gram)/Melting Point |
|---|---|---|---|---|---|
| 26 | (structure: valine methyl ester with N-methyl) | -chloride 5.23 | NEt₃ 3.48 | THF, 150 | (2,3-dibromothenoyl)-N-methyl-valine methyl ester |
| 27 | (structure: valine amide) 50 | -chloride 99.7 | NaHCO₃ 55 | H₂O, 1500 THF, 700 | (2,3-dibromothenoyl)-L-valine amide 120/238–240° C. |
| 28 | (structure: valine isobutylamide) 3.98 | -chloride 5.23 | NaHCO₃ 2.88 | H₂O, 100 THF, 50 | (2,3-dibromothenoyl)-L-valine isobutylamide 7.23/206–209° C. |
| 29 | (structure: N-methyl valine amide) 2.87 | -chloride 5.23 | NaHCO₃ 2.88 | H₂O, 100 THF, 50 | (2,3-dibromothenoyl)-N-methyl-L-valine amide 5.79/150–152° C. |
| 30 | (structure: valine N-methylamide) 2.0 (as acetate) | -chloride 3.2 | NaHCO₃ 1.77 | H₂O, 100 THF, 35 | (2,3-dibromothenoyl)-L-valine N-methylamide 3.98/230–231° C. |

EXAMPLE 31

4.0 g 2,3-dibromothiophene-5-carboxylic acid bromide dissolved in 50 ml THF are added drop-by-drop to a suspension of 2.89 g L-valine anilide acetate and 2.31 g triethyl amine in 100 ml THF at 25° C. within 3 hours. The thick suspension obtained in this manner is agitated a further 2 hours at this temperature, filtered and the filtrate concentrated by evaporation at 40 mbars. The residue obtained in this manner is washed twice with 30 ml H₂O and after filtration with 50 ml petroleum ether (50°–90° C.) and then dried at 50° C. to constant weight.

$N_\alpha$-(2',3'-dibromo-5'-thenoyl)-L-valine anilide with a melting point of 195°–198° C. are obtained.

EXAMPLE 32

4.0 g 2,3-dibromothiophene-5-carboxylic acid bromide are reacted in a manner analogous to Example 31 with 2.94 g L-leucine anilide acetate.

After workup, 2.5 g (50% of theory) $N_\alpha$-(2',3'-dibromo-5'-thenoyl)-L-leucine anilide with a melting point of 210°–212° C. are obtained.

EXAMPLE 33

A suspension of 1.59 g L-valine amide•HCl and 2.31 g triethyl amine in 100 ml THF are reacted in a manner analogous to Example 31 with a solution of 4.0 g 2,3-dibromothiophene-5-carboxylic acid in 25 ml THF.

After workup, 3.27 g (74.2% of theory) $N_\alpha$-(2',3'-dibromo-5'-thenoyl)-L-valine amide with a melting point of 235°–240° C. are obtained.

EXAMPLE 34

5.23 g 2,3-dibromothiophene-5-carboxylic acid chloride in 50 ml THF are added drop-by-drop into a suspension of 3.81 g L-hexahydrophenylalanine methyl ester•HCl and 2.88 g NaHCO₃ in 100 ml water at 10° C. within one hour.

After a further 2 hours of agitation, the separated oil is taken up in 100 ml ethyl acetate, dried over Na₂SO₄ and the solvent distilled off. The viscous residue is freed of solvent remnants at 0.1 mbar and 50° C. 6.3 g (80.1% of theory) N-(2,,3,-dibromo-5'-thenoyl)-L-hexahydrophenyl alanine methyl ester is obtained as a viscous oil.

EXAMPLE 35

A solution of 15.3 g 2,3,4-tribromothiophene carboxylic acid chloride in 50 ml THF is added drop-by-drop to a solution of 6.71 g L-valine methyl ester•HCl in 50 ml pyridine within 30 min. at 20° C. After a subsequent two hours of agitation at the same temperature, the precipitated salts are filtered off and the residue washed neutral with 3 times with 20 ml H₂O. It is taken up in 200 ml hot acetone, compounded with 5 g activated carbon and filtered off via a pressure filter. When the clarified solution is concentrated by evaporation, 10.8 g (56.4% of theory) N-(2',3',4'-tribromothenoyl)-L-valine methyl ester with a melting point of 110°–112° C. are obtained.

EXAMPLE 36

4.36 g DL-valine methyl ester•HCl in 30 ml pyridine are reacted in a manner analogous to Example 35 with a solution of 10 g 2,3,4-tribromothiophene carboxylic acid chloride in 30 ml THF.

After recrystallization from a 1:1 mixture of petroleum ether/Et₂O, 1.7 g (13.7% of theory) N-(2',3',4'-tribromothenoyl)-DL-valine methyl ester with a melting point of 85°–88° C. are obtained.

EXAMPLE 37

5.66 g L-leucine methyl ester•HCl in 30 ml pyridine are reacted in a manner analogous to Example 35 with 15 g 2,3,4-tribromothiophene carboxylic acid chloride in 40 ml THF.

After workup, 4.8 g (25% of theory) N-(2',3',4'-tribromothenoyl)-L-leucine methyl ester with a melting point of 70°–73° C. are obtained.

EXAMPLE 38

7.26 g L-valine ethyl ester•HCl in 50 ml pyridine are reacted in a manner analogous to Example 35 with 15.3 g 2,3,4-tribromothiophene carboxylic acid chloride in 50 ml THF.

After workup, 11.8 g (60% of theory) N-(2',3',4'-tribromothenoyl)-L-valine ethyl ester with a melting point of 102°–105° C. are obtained.

EXAMPLE 39

8.3 g 1 amino cycloheptane carboxylic acid methyl ester•HCl in 50 ml pyridine are reacted according to Example 35 with 15.3 g 2,3,4-tribromothiophene carboxylic acid chloride in 50 ml THF.

After workup, 8.1 g (39.0% of theory) N-(2',3',4'-tribromothenoyl)-1-amino cycloheptane carboxylic acid methyl ester with a melting point of 165°–68° C. are obtained.

EXAMPLE 40

2.23 g 2,3-dibromothiophene-5-carboxylic acid chloride in 40 ml dioxane are added drop-by-drop into a solution of 2.27 g KOH and 2.25 g N-methyl-DL-valine in 100 ml H₂O at 20° C. within 2 hours. After a further reaction of one hour, the mixture is acidified with HCl to pH 2, the organic phase separated and condensed by evaporation. The residue is crystallized with 30 ml diisopropyl ether 5 14 g (74.9% of theory) N-2',3'-dibromo-5'-thenoyl)-N-methyl-DL-valine with a melting point of 160°–163° C. are obtained.

EXAMPLE 41

5.0 g 2,3,4-tribromothiophene carboxylic acid chloride dissolved in 50 ml THF are added drop-by-drop to a suspension of 3.29 g L-tert.-leucine-2',2',2'-trifluoroethyl ester•HCl and 2.63 g triethyl amine in 100 ml THF within 3 hours at 20° C. The thick suspension obtained in this manner is agitated a further 2 hours at this temperature, filtered and the filtrate concentrated by evaporation at 40 mbars. The residue obtained in this manner is washed twice with 30 ml H₂O and then with 50 ml petroleum ether/Et₂O and dried to constant weight.

5.26 g (72% of theory) N-(2',3',4'-tribromothenoyl)-L-tert.-leucine-2",2",2"-trifluoroethyl ester with a melting point of 93°–95° C. are obtained.

Examples 42–70 are carried out in a manner analogous to Example 41 (See Table 2.)

TABLE 2

| Example | As-Ester.HCl o.Amide.HCl | 2.3.4.-Tribromthiophen-carbonyl chloride [g] | NEt₃ [g] | Solvent [ml] | Product/Melting Point |
|---|---|---|---|---|---|
| 42 | 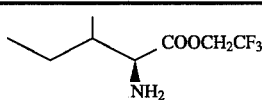 3.29 | 5.0 | NEt₃ 2.63 | THF, 150 | 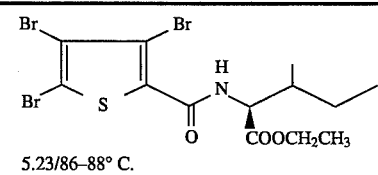 5.23/86–88° C. |
| 43 | 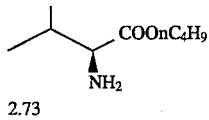 2.73 | 5.0 | NEt₃ 2.63 | THF, 150 | 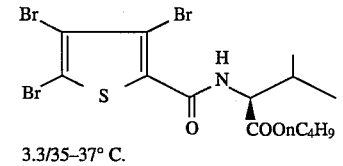 3.3/35–37° C. |

TABLE 2-continued

| Example | As-Ester.HCl o.Amide.HCl | 2.3.4.-Tribromthiophencarbonyl chloride [g] | NEt₃ [g] | Solvent [ml] | Product/Melting Point |
|---|---|---|---|---|---|
| 44 | CH₃-CH(CH(CH₃)₂)(COOCH₃)(NH₂) 2.73 | 5.75 | NEt₃ 3.03 | THF, 100 | 2,3,4-tribromothiophene-5-carboxamide with H₃C-C(CH(CH₃)₂)(COOCH₃)NH- 4.94/92–95° C. |
| 45 | 1-amino-1-cyclohexyl-COOCH₃ 2.01 | 5.0 | NEt₃ 2.63 | THF, 150 | tribromothiophene-carboxamide-cyclohexyl-COOCH₃ 3.75/147–149° C. |
| 46 | (CH₃)₂CHCH₂-CH(NH₂)COOCH₂CF₃ 3.29 | 5.0 | NEt₃ 2.63 | THF, 150 | tribromothiophene-carboxamide-CH(CH₂CH(CH₃)₂)COOCH₃CF₃ 4.71/88–90° C. |
| 47 | (CH₃)₂CH-CH(NH₂)COOCH₂CF₃ 2.36 | 3.83 | NEt₃ 2.02 | THF, 150 | tribromothiophene-carboxamide-CH(CH(CH₃)₂)COOCH₂CF₃ 3.54/123–124° C. |
| 48 | H₂N—CH₂—COOCH₃ 1.64 | 5.0 | NEt₃ 2.63 | THF, 150 | tribromothiophene-carboxamide-NH-CH₂-COOCH₃ 5.23/145–147° C. |
| 49 | PhCH₂-CH(NH₂)COOCH₃ 2.25 | 4.0 | NEt₃ 2.10 | THF, 150 | tribromothiophene-carboxamide-CH(CH₂Ph)COOCH₃ 4.16/136–138° C. |
| 50 | cyclopropyl-CH(NH₂)COOCH₃ 1.9 | 4.39 | NEt₃ 2.32 | THF, 100 | tribromothiophene-carboxamide-CH(cyclopropyl)COOCH₃ 2.61/120–122° C. |
| 51 | cyclopropyl-CH(NH₂)COOCH₃ 2.5 | 5.5 | NEt₃ 3.05 | THF, 70 | tribromothiophene-carboxamide-NH-CH(cyclopropyl)COOCH₃ 5.35/104–106° C. |

TABLE 2-continued

| Example | As-Ester.HCl o.Amide.HCl | 2.3.4.-Tribrom-thiophen-carbonyl chloride [g] | NEt₃ [g] | Solvent [ml] | Product/Melting Point |
|---|---|---|---|---|---|
| 52 | H₂N—CH₂—C(=O)—NHCH₃<br>2.43 | 7.5 | NEt₃ 3.95 | THF, 150 | [2,4,5-tribromothiophene-3-carbonyl]-NH-CH₂-CONHCH₃<br>4.28/237–239° C. |
| 53 | Valine amide (CONH₂, NH₂)<br>1.06 | 2.93 | NEt₃ 1.54 | THF, 150 | Tribromothiophene-carbonyl-valine amide<br>2.56/205–206° C. |
| 54 | Valine anilide (CONHC₆H₅, NH₂)<br>als Acetat 3.29 | 5.0 | NEt₃ 2.63 | THF, 150 | Tribromothiophene-carbonyl-valine anilide<br>3.87/224–226° C. |
| 55 | Leucine anilide (CONHC₆H₅, NH₂)<br>als Acetat 3.47 | 5.0 | NEt₃ 2.63 | THF, 150 | Tribromothiophene-carbonyl-leucine anilide<br>3.0/190–192° C. |
| 56 | Isoleucine methyl ester (COOCH₃, NH₂)<br>7.08 | 15.0 | NEt₃ 7.89 | THF, 150 | Tribromothiophene-carbonyl-isoleucine methyl ester<br>15.1/84–86° C. |
| 57 | H₂N–CH₂–C(=O)–O–iPr<br>6.0 | 15.0 | NEt₃ 7.89 | THF, 150 | Tribromothiophene-carbonyl-glycine isopropyl ester<br>15.46/113–116° C. |
| 58 | Methionine methyl ester (S-CH₃, COOCH₃, NH₂)<br>8.68 | 15.0 | NEt₃ 7.89 | THF, 150 | Tribromothiophene-carbonyl-methionine methyl ester<br>15.0/80–82° C. |
| 59 | tert-Leucine methyl ester (COOCH₃, NH₂)<br>7.08 | 15.0 | NEt₃ 7.89 | THF, 150 | Tribromothiophene-carbonyl-tert-leucine methyl ester<br>15.9/117–120° C. |

TABLE 2-continued

| Example | As-Ester·HCl o.Amide·HCl | 2.3.4.-Tribromthiophen-carbonyl chloride [g] | NEt₃ [g] | Solvent [ml] | Product/Melting Point |
|---|---|---|---|---|---|
| 60 | (CH₃)₂CH-C(D)(NH₂)-COOCH₃ · HCl, 6.54 | 15.0 | NEt₃ 7.89 | THF, 150 | 2,3,4-tribromothiophene-5-carboxamide of (D)-valine methyl ester, 14.9 / 107–110° C. |
| 61 | (CH₃)₂C(NH₂)-COOCH₃ · HCl, 4.02 | 15.0 | NEt₃ 7.89 | THF, 150 | 2,3,4-tribromothiophene-5-carboxamide of α-aminoisobutyric acid methyl ester, 8.91 / 128–130° C. |
| 62 | H₃COOC-CH₂-CH₂-CH(NH₂)-COOCH₃ · HCl, 2.76 | 5.0 | NEt₃ 2.63 | THF, 150 | 2,3,4-tribromothiophene-5-carboxamide of glutamic acid dimethyl ester, 4.9 / 118–120° C. |
| 63 | H₃C-NH-CH₂-COOC₂H₅ · HCl, 2.0 | 5.0 | NEt₃ 2.63 | THF, 150 | 2,3,4-tribromothiophene-5-carboxamide of sarcosine ethyl ester, 4.56 / 78–80° C. |
| 64 | CH₃CH₂-CH(NH₂)-COOCH₃ · HCl, 2.0 | 5.0 | NaHCO₃ 2.19 | H₂O, 100 THF, 50 | 2,3,4-tribromothiophene-5-carboxamide of (S)-2-aminobutyric acid methyl ester, 4.97 / 122–124° C. |
| 65 | CH₃CH₂CH₂-CH(NH₂)-COOCH₃ · HCl, 2.19 | 5.0 | NEt₃ 2.63 | THF, 150 | 2,3,4-tribromothiophene-5-carboxamide of norvaline methyl ester, 4.75 / 105–107° C. |
| 66 | CH₃(CH₂)₃-CH(NH₂)-COOCH₃ · HCl, 2.37 | 5.0 | NEt₃ 2.63 | THF, 150 | 2,3,4-tribromothiophene-5-carboxamide of norleucine methyl ester, 5.03 / 102–104° C. |
| 67 | (CH₃)₂CH-CH(NHCH₃)-COOCH₃ · HCl, — | 5.0 | NEt₃ 2.63 | THF, 150 | 2,3,4-tribromothiophene-5-carboxamide of N-methyl-valine methyl ester |

TABLE 2-continued

| Example | As-Ester.HCl o.Amide.HCl | 2.3.4.-Tribromthiophen-carbonyl chloride [g] | NEt₃ [g] | Solvent [ml] | Product/Melting Point |
|---|---|---|---|---|---|
| 68 | (structure: L-valine isobutylamide) 3.98 | 6.59 | NaHCO₃ 2.88 | H₂O, 100 THF, 50 | (tribromothienoyl-L-valine isobutylamide) 6.38/195–197° C. |
| 69 | (structure: N-methyl-valinamide) 2.17 | 5.0 | NaHCO₃ 2.88 | H₂O, 100 THF, 50 | (product structure) 4.55/208–211° C. |
| 70 | (structure: valine N-methylamide) 2.0 (As acetate) | 4.02 | NaHCO₃ 2.19 | H₂O, 100 THF, 40 | (product structure) 3.44/250–252° C. |

EXAMPLE 71

4.0 g 2,3-dichlorothiophene-5-carboxylic acid chloride in 50 ml THF are added drop-by-drop to a suspension of 3.37 g L-leucine methyl ester•HCl and 3.76 g triethyl amine in 100 ml THF at 20° C. within 3 hours. The mixture is then agitated 2 hours, filtered from the precipitated salts, the filtrate concentrated by evaporation and the residue thoroughly agitated with twice 30 ml H₂O, then washed with petroleum ether and dried at 40° C./40 mbars to constant weight.

5.25 g (87% of theory) N-2',3'-dichloro-5'-thenoyl)-L-leucine methyl ester with a melting point of 93°–95° C. are obtained.

EXAMPLE 72

4.0 g 2,3-dichlorothiophene-5-carboxylic acid chloride are reacted in a manner analogous to Example 71 with 3.37 g L-isoleucine methyl ester•HCl.

After workup, 3.76 g (62.3% of theory) N-2',3'-dichloro-5'-thenoyl)-L-isoleucine methyl ester with a melting point of 48°–50° C. are obtained.

EXAMPLE 73

4.0 g L-valine methyl ester•HCl are reacted in a manner analogous to Example 71 with 5.14 g 2,3-dichlorothiophene-5-carboxylic acid chloride.

After workup, 5.11 g (69% of theory) N-(2',3'-dichloro-5'-thenoyl)-L-valine methyl ester with a melting point of 75°–76° C. are obtained.

EXAMPLE 74

2.74 g 2,3-dichlorothiophene-5-carboxylic acid chloride are reacted in a manner analogous to Example 71 with 3.0 g L-valine-2',2',2'-trifluoroethyl ester•HCl.

After workup, 4.14 g (86.1% of theory) N-(2',3'-dichloro-5'-thenoyl)-L-valine-2",2",2"-trifluoroethyl ester with a melting point of 53°–54° C. are obtained.

EXAMPLE 75

2.81 g 2,3-dichlorothiophene-5-carboxylic acid chloride are reacted in a manner analogous to Example 71 with 3.29 g L-leucine-2',2',2'-trifluoroethyl ester•HCl.

After workup, 3.27 g (65% of theory) N-(2',3'-dichloro-5'-thenoyl)-L-leucine-2",2",2"-trifluoroethyl ester with a melting point of 68°–70° C. are obtained.

EXAMPLE 76

3.29 g L-isoleucine-2',2',2'-trifluoroethyl ester•HCl are reacted in a manner analogous to Example 71 with 2.81 g 2,3-dichlorothiophene-5-carboxylic acid chloride.

After workup, 4.1 g (65.4% of theory) N-(2',3'-dichloro-5'-thenoyl)-L-isoleucine-2",2",2"-trifluoroethyl ester with a melting point of 73°–75° C. are obtained.

EXAMPLE 77

5.00 g 2,3,4-tribromothiophene-carboxylic acid chloride are reacted in a manner analogous to Example 71 with 2.89 g L-hexahydro-phenylalanine methyl ester•HCl and 2.63 g triethyl amine in 150 ml THF.

After workup, 4.2 g (61.2% of theory) N-(2',3',4'-tribromothenoyl)-L-hexahydrophenyl alanine methyl ester are obtained as a viscous oil.

EXAMPLE 78

12.0 g 2,3-dichlorothiophene-5-carboxylic acid chloride are added drop-by-drop into a solution of 4.45 g NaOH and 4.95 g DL-alanine in 60 ml water at 10° C. After the end of the reaction, the mixture is agitated 1 hour more and then acidified to pH 2 with conc. HCl. The separated oil is taken up in 100 ml ethyl acetate, washed neutral twice with 20 ml water and the solvent is distilled off after drying. The viscous residue crystallized after mixing with 30 ml diisopropyl ether. After drying at 40° C./50 mbars until the weight was constant, 14.0 g (99.6% of theory) N-(2',3'-dichloro-5'-thenoyl)-DL-alanine with a melting point of 195°–197° C. are obtained.

EXAMPLE 79

12.0 g 2,3-dichlorothiophene-5-carboxylic acid chloride are reacted in a manner analogous to Example 78 with 4.95 g L-alanine.

After workup, 13.75 g (98.1% of theory) N-(2',3'-dichloro-5'-thenoyl)-L-alanine with a melting point of 198°–202° C. are obtained.

EXAMPLE 80

12.0 g 2,3-dichlorothiophene-5-carboxylic acid chloride are reacted in a manner analogous to Example 78 with 4.95 g D-alanine.

After workup, 13.0 g (92.6% of theory) N-(2',3'-dichloro-5'-thenoyl-D-alanine with a melting point of 198°–200° C. are obtained.

EXAMPLE 81

10.8 g 2,3-dichlorothiophene-5-carboxylic acid chloride are reacted in a manner analogous to Example 78 with 5.86 g DL-valine and 4.0 g NaOH in 60 ml water.

After workup, 10.0 g (67.6% of theory) N-(2',3'-dichloro-5'-thenoyl)-D,L-valine with a melting point of 188°–190° C. are obtained.

EXAMPLE 82

12.0 g 2,3-dichlorothiophene-5-carboxylic acid chloride are reacted in a manner analogous to Example 78 with 5.73 g DL-α-amino butyric acid and 4.45 g NaOH in 60 ml water.

After workup, 13.74 g (85.7% of theory) N-(2',3'-dichloro-5'-thenoyl)-DL-α-amino butyric acid are obtained.

EXAMPLE 83

12.0 g 2,3-dichlorothiophene-5-carboxylic acid chloride are reacted in a manner analogous to Example 78 with 5.73 g α-amino isobutyric acid and 4.45 g NaOH in 60 ml $H_2O$.

After being worked up with diethyl ether, 7.38 g (47% of theory) N-(2',3'-dichloro-5'-thenoyl)-α-amino isobutyric acid with a melting point of 217°–220° C. are obtained.

EXAMPLE 84

10.8 g 2,3-dichlorothiophene-5-carboxylic acid chloride are reacted in a manner analogous to Example 78 with 7.4 g DL-methionine and 4.0 g NaOH in 50 ml $H_2O$.

After workup, 16.0 g (97.5% of theory) N-(2',3'-dichloro-5'-thenoyl)-DL-methionine with a melting point of 193°–195° C. are directly obtained.

EXAMPLE 85

10.8 g 2,3-dichlorothiophene-5-carboxylic acid chloride are reacted in a manner analogous to Example 78 with 3.8 g glycine and 4.0 g NaOH in 50 ml $H_2O$.

After workup and recrystallization from ethyl acetate, 6.2 g (48.8% of theory) N-(2',3'-dichloro-5'-thenoyl)glycine with a melting point of 212°–214° C. are obtained.

EXAMPLE 86

10.8 g 2,3-dichlorothiophene-5-carboxylic acid chloride are reacted in a manner analogous to Example 78 with 7.36 g L-glutamic acid and 6.0 g NaOH in 60 ml $H_2O$.

After workup, 9.82 g (60.2% of theory) N-(2',3'-dichloro-5'-thenoyl)-L-glutamic acid with a melting point of 150°–157° C. are obtained.

EXAMPLE 87

10.8 g 2,3-dichlorothiophene-5-carboxylic acid chloride are reacted in a manner analogous to Example 78 with 6.56 g L-isoleucine and 8.4 g $NaHCO_3$ in 60 ml $H_2O$.

After workup, 6.91 g (44.5% of theory) N-(2',3'-dichloro-5'-thenoyl)-L-isoleucine with a melting point of 130°–135° C. are obtained.

EXAMPLE 88

10.24 g 2,3-dichlorothiophene-5-carboxylic acid chloride are reacted in a manner analogous to Example 78 with 6.32 g L-thiazolidine-4-carboxylic acid and 7.98 g $NaHCO_3$ in 100 ml $H_2O$.

After workup, 4.0 g (27.3% of theory) N-(2',3'-dichloro-5'-thenoyl)-L-thiazolidine-4-carboxylic acid with a melting point of 195°–200° C. are obtained.

EXAMPLE 89

4.5 g DL-alanine are dissolved together with 4.0 g NaOH in 40 ml $H_2O$. A solution of 10.8 g 2,3-dibromothiophene-5-carboxylic acid chloride in 10 ml toluene is added drop-by-drop to this solution at 50° C. and allowed to react for 1 hour. After phase separation, the aqueous phase is acidified to pH 2 with conc. HCl and the oil which separates is crystallized after a short period of standing. The solid matter is removed by suction, washed neutral with $H_2O$ and dried at 50° C./50 mbars to constant weight.

12.1 g (96.8% of theory) N-(2',3'-dibromo-5'-thenoyl)-DL-alanine with a melting point of 205°–208° C. are obtained.

EXAMPLE 90

15.3 g 2,3,4-tribromothiophene carboxylic acid chloride in 60 ml dioxane are reacted in a manner analogous to Example 89 with 34.56 g L-alanine and 3.20 g NaOH in 60 ml $H_2O$. After workup, 10.5 g (60.1% of theory) N-(2',3',4'-tribromothenoyl)-L-alanine with a melting point of 175°–179° C. are obtained.

EXAMPLE 91

15.3 g 2,3,4-tribromothiophene carboxylic acid chloride in 60 ml dioxane are reacted in a manner analogous to Example 89 with 4.69 g L-valine and 3.20 g NaOH in 60 ml $H_2O$.

After workup, 11.7 g (63.1% of theory) N-(2',3',4'-tribromothenoyl)-L-valine with a melting point of 137°–140° C. are obtained.

EXAMPLE 92

10 g 2,3,4-trichlorothiophene carboxylic acid chloride in 50 ml THF are reacted in a manner analogous to Example 89 with 3.56 g L-alanine and 3.20 g NaOH in 60 ml $H_2O$.

EXAMPLE 93

10 g 2,3,4-trichlorothiophene carboxylic acid chloride in 50 ml THF are reacted in a manner analogous to Example 89 with 4.69 g L-valine and 3.20 g NaOH in 60 ml H$_2$O.

After workup, 10.2 g (84.5% of theory) N-(2',3',4'-trichlorothenoyl)-L-alanine with a melting point of 160°–164° C. are obtained.

After workup, 11.9 g (90% of theory) N-(2',3',4'-trichlorothenoyl)-L-valine with a melting point of 120°–123° C. are obtained.

EXAMPLE 94

10.8 g 2,3-dichlorothiophene-5-carboxylic acid chloride are reacted in a manner analogous to Example 78 with 6.56 g L-leucine and 8.4 g NaHCO$_3$ in 60 ml water.

After workup, 9.11 g (61.1% of theory) N-(2',3'-dichloro-5'-thenoyl)-L-leucine with a melting point of 125°–135° C. are obtained.

EXAMPLE 95

2.01 g L-valine, 2.27 g KOH and 5.23 g 2,3-dibromothiophene-5-carboxylic acid chloride are reacted in a manner analogous to Example 40.

After workup, 5.3 g (80.0% of theory) N-(2',3'-dibromo-5'-thenoyl)-L-valine with a melting point of 169°–173° C. are obtained.

EXAMPLE 96

10.0 g 2,3,4-trichlorothiophene carboxylic acid chloride in 50 ml THF are added drop-by-drop to a solution of 7.62 g L-valine ethyl ester•HCl in 50 ml pyridine at 20° C. within 2 hours. The mixture is then agitated 2 hours, the solvent concentrated by evaporation and the residue thoroughly agitated twice with 30 ml water per time. The crystals which precipitate are filtered off, washed neutral with more water and dried at 50° C./40 mbars to constant weight.

11.35 g (79.1% of theory) N-(2',3',4-trichlorothenoyl)-L-valine ethyl ester with a melting point of 66°–68° C. are obtained.

EXAMPLE 97

10 g 2,3,4-trichlorothiophene carboxylic acid chloride are reacted in a manner analogous to Example 96 with 6.71 g L-valine methyl ester•HCl.

After workup, 9.9 g (71.7% of theory) N-(2',3',4'-trichlorothenoyl)-L-valine methyl ester with a melting point of 47°–50° C. are obtained.

EXAMPLE 98

15 g 2,3,4-tribromothiophene carboxylic acid chloride are reacted in a manner analogous to Example 58 with 8.68 g L-methionine ethyl ester•HCl.

After workup, 15.0 g (73.4% of theory) N-(2',3',4'-tribromothenoyl)-L-methionine ethyl ester with a melting point of 80°–82° C. are obtained.

EXAMPLE 99

15.3 g 2,3,4-tribromothiophene carboxylic acid chloride are reacted in a manner analogous to Example 58 with 5.58 g L-alanine ethyl ester•HCl.

After workup, 4.6 g (25.5% of theory) N-(2',3',4'-tribromothenoyl)-L-alanine ethyl ester with a melting point of 112°–114° C. are obtained.

EXAMPLE 100

15.0 g 2,3-dibromothiophene-5-carboxylic acid chloride are reacted in a manner analogous to Example 71 with 9.6 g L-methionine ethyl ester•HCl.

After workup, 14.5 g (76% of theory) N-(2',3'-dibromo-5'-thenoyl)-L-methionine ethyl ester is obtained as a viscous oil.

BIOLOGICAL EXAMPLES

Example 1: Action against *Colletotrichum lagenarium* on cucumbers (*Cucumis sativus L*)

a) Cucumbers are sprayed after 2 weeks of cultivation with a spray mixture produced from wettable powder of the active ingredient (concentration: 200 ppm).

After 48 hours, the plants are infected with a spore suspension (1.5·10$^3$ spores/ml) of the fungus and incubated 36 hours at high air moisture and a temperature of 23° C. The incubation is then continued at normal air moisture and at 22° C. to 23° C.

The evaluation of the protective action takes place based on the fungus attack 7–8 days after the infection.

b) Cucumbers are treated after 2 weeks of cultivation by means of soil application with a spray mixture produced from wettable powder of the active ingredient (concentration: 60 or 20 ppm relative to the soil volume).

After 48 hours, the plants are infected with a spore suspension (1.5·10$^3$ spores/ml) of the fungus and incubated 36 hours at high air moisture and a temperature of 23° C. The incubation is then continued at normal air moisture and at 22° C.

The evaluation of the protective action takes place based on the fungus attack 7–8 days after the infection.

Untreated but infected reference plants exhibit a fungus attack of 100% in tests a) and b).

Compounds in accordance with the present invention provide good protection against *Colletotrichum lagenarium*. Thus, plants which were treated e.g. with the compounds of Examples No. 4, 11, 13, 84, 85, 89, 91, 92, 93 and 96 remain largely free of Colletotrichum (attack 0–20%).

Example 2: Action against *Puccinia graminis* on wheat a) Wheat plants are sprayed 6 days after sowing with a spray mixture produced from wettable powder of the active ingredient (0.02 active substance). After 24 hours, the treated plants are infected with a suspension of uredospores of the fungus. After an incubation during 48 hours at 95–100% relative humidity and approximately 20° C., the infected plants are placed in a greenhouse at approximately 22° C. The evaluation of the development of rust vesicles takes place 12 days after the infection.

b) A spray mixture produced from wettable powder of the active ingredient (0.006% active substance relative to the soil volume) is poured onto wheat plants 5 days after sowing. After 48 hours, the treated plants are infected with a suspension of uredospores of the fungus. After an incubation during 48 hours at 95–100% relative humidity and approximately 20° C., the infected plants are placed in a greenhouse at approximately 22° C. The evaluation of the development of rust vesicles takes place 12 days after the infection.

Untreated but infected reference plants exhibit a fungus attack of 100% in tests a) and b).

Compounds in accordance with the present invention provide good protection against Puccinia graminis. Thus, plants which were treated e.g. with the compounds of Examples No. 9, 71, 72, 75, 76 and 85 remain largely free of Puccinia (attack 0–20%).

Example 3 Action against *Phytophthora infestans* on tomato plants a) Tomato plants are sprayed after 3 weeks of cultivation with a spray mixture produced from wettable powder of the active ingredient (0.02 active substance). After 24 hours, the treated plants are infected with a suspension of sporangia of the fungus. The evaluation of the fungus attack took place after an incubation of the infected plants during 5 days at 90°–100° C. relative humidity and 20° C.

b) A spray mixture produced from wettable powder of the active substance is poured on tomato plants after 3 weeks of cultivation (0.006% active substance relative to the volume of soil). Care is taken that the spray mixture does not come in contact with the plant parts which are above the ground. After 48 hours, the treated plants are infected with a suspension of sporangia of the fungus. The evaluation of the fungus attack took place after an incubation of the infected plants during 5 days at 90°–100° C. relative air moisture and 20° C.

Untreated but infected reference plants exhibit a fungus attack of 100% in tests a) and b).

Compounds in accordance with the present invention provide good protection against *Phytophthora infestans*. Thus, plants which were treated e.g. with the compounds of Examples No. 1, 3, 4, 10, 11, 13, 27, 37, 48, 50, 73, 79, 80, 81, 82, 83, 85, 86, 87, 90, 92, 96, 97 and 99 remain largely free of *Phytophthora* (attack 0°–20%).

Example 4: Action against *Pyricularia oryzae* on rice plants a) Rice plants are sprayed after 2 weeks of cultivation with a spray mixture produced from wettable powder of the active ingredient (0.02 active substance). After 48 hours, the treated plants are infected with a suspension of conidia of the fungus. The evaluation of the fungus attack took place after an incubation of the infected plants during 5 days at 95°–100° C. relative humidity and 24° C.

b) A spray mixture produced from wettable powder of the active substance is poured on two-week-old rice plants (0.006% active substance relative to the volume of soil). Then, the pots are filled with water until the lowest stalk parts of the rice plants are standing in water. After 96 hours, the treated rice plants are infected with a suspension of conidia of the fungus.

The evaluation of the fungus attack took place after an incubation of the infected plants during 5 days at 90°–100° C. relative humidity and approximately 24° C.

Untreated but infected reference plants exhibit a fungus attack of 100% in tests a) and b).

Compounds in accordance with the present invention provide good protection against Pyricularia oryzae. Thus, plants which were treated e.g. with the compounds of Examples No. 3, 4, 13, 27, 49, 73, 76, 78, 79, 80, 83 and 87 remain largely free of Pyricularia (attack 0–20%).

Example 5: Action against Pseudomonas tomato on tomato plants a) Tomato plants are treated by leaf application after 3 weeks of cultivation with a spray mixture produced from wettable powder of the active ingredient (concentration 200 ppm). After 3.5 weeks, the plants are inoculated with a bacterial suspension ($10^8$ bacteria/ml) and incubated for 5 days at high humidity and at a temperature of 25° C. The evaluation of the protective action takes place based on the bacterial attack 7–8 days after inoculation.

b) Tomato plants are treated by leaf application after 3 weeks of cultivation with a spray mixture produced from wettable powder of the active ingredient (concentration 60 ppm relative to the soil volume). After 3.5 weeks, the plants are inoculated with a bacterial suspension ($10^8$ bacteria/ml) and incubated for 6 days at high humidity and at a temperature of 25° C. The evaluation of the protective action takes place based on the bacterial attack 7–8 days after inoculation.

Untreated but infected reference plants exhibit a fungus attack of 100% in tests a) and b).

Compounds in accordance with the present invention provide good protection against Pseudomonas tomato. Thus, plants which were treated e.g. with the compounds of Examples No. 1, 6, 16, 18, 35, 38, 48, 51, 73, 98 and 100 remain largely free of *Pseudomonas* (attack 0–20%).

Example 6: Action against *Xanthomonas oryzae* on rice (*Oryza sativa*)

a) Rice plants of the "calora" or "S6" type are sprayed after 3 weeks of cultivation in a greenhouse with the test substance in the form of a spray mixture (0.02% active substance). After this sprayed coating has dried for one day, the plants are placed in a controlled environment chamber at 24° C. and with 75–85% relative humidity and infected. The infection takes place by cutting off the leaf tips with scissors which had previously been dipped into a suspension of *Xanthomonas oryzae*. After 10 days of incubation, the cut leaves become wilted upon attack, curl up and become necrotic. The extent of these symptoms of disease serves as an evaluation of the residual activity of the test substance.

b) Rice plants of the "calora" or "S6" type are sprayed after 3 weeks of cultivation in a greenhouse with the test substance in the form of a spray mixture (0.006% active substance relative to the soil volume). Three days after this treatment, the plants are placed in a controlled environment chamber at 24° C. and with 75–85% relative humidity and infected. The infection takes place by cutting off the leaf tips with scissors which had previously been dipped into a suspension of Xanthomonas oryzae. After 10 days of incubation, the cut leaves become wilted upon attack, curl up and become necrotic. The extent of these symptoms of disease serves for an evaluation of the systemic activity of the test substance.

Untreated but infected reference plants exhibit a fungus attack of 100% in tests a) and b).

Compounds in accordance with the present invention provide good protection against *Xanthomonas oryzae*. Thus, plants which were treated e.g. with the compounds of Examples No. 1, 4, 16, 18, 19, 27, 35, 38, 51, 73, 84 and 100 remain largely free of Xanthomonas (attack 0–20%).

Example 7: Action against *Xanthomonas versicatoria* on pepper (*Capsicum annuum*)

a) Pepper plants of the "California Wonder" type are sprayed after 3 weeks of cultivation in a greenhouse with the test substance in the form of a spray mixture (0.02% active substance). After this sprayed coating has dried for one day, the plants are placed in a controlled environment chamber at 26° C. and with 95–100% relative humidity and infected by spraying the underside of the leaves with a standardized suspension of *Xanthomonas versicatoria*. After 6 days of incubation, round, initially watery, later necrotic, bright spots form on the leaves upon attack. The extent of these symptoms of disease serves for an evaluation of the residual activity of the test substance.

b) A suspension of the test substance is poured on pepper plants of the "California Wonder" type after 3 weeks of cultivation in a greenhouse (0.006% active substance relative to the soil volume). Three days after this treatment, the plants are placed in a controlled environment chamber at 26° C. and with 95–100% relative humidity and infected by spraying the underside of the leaves with a standardized suspension of *Xanthomonas versicatoria*. After 6 days of incubation, round, initially watery, later necrotic, bright spots form on the leaves upon attack. The extent of these symptoms of disease serves for an evaluation of the systemic activity of the test substance.

Untreated but infected reference plants exhibit a fungus attack of 100% in tests a) and b). Compounds in accordance with the present invention provide good protection against *Xanthomonas versicatoria*. Thus, plants which were treated e.g. with the compounds of Examples No. 1, 4, 6, 7, 16, 18, 19, 27, 28, 31, 35, 38, 56, 73 and 84 remain largely free of Xanthomonas (attack 0–20%).

What is claimed is:

1. A method of treating plants to provide protection against phytopathogenic microorganisms which comprises applying to the plants, their plant parts or the site of their growth an effective amount of a compound of the general formula I:

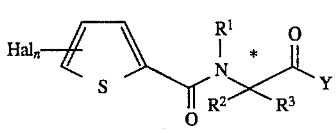

I wherein Hal is chlorine or bromine, n is the number 2 or 3, and $R^2$ and $R^3$ can be the same or different, and includes all possible isomers at *, $R^1$ is (1) hydrogen, (2) a straight-chain alkyl group having 1–4 carbon atoms or (3) a branched-chain alkyl group having 3–4 carbon atoms, $R^2$ is (1) hydrogen, (2) a straight-chain alkyl group having 1–16 carbon atoms or (3) a branched-chain alkyl group having 3–16 carbon atoms, wherein (2) and/or (3) can be substituted by hydroxy-, carboxy-, $C_1$–$C_6$ alkoxy-or $C_1$–$C_6$ alkoxycarbonyl, mercapto- or $C_1$–$C_6$ alkylmercapto- orbenzylmercapto, (4) an aryl group having 6–10 carbon atoms or (5) an aralkyl group with 7–16 carbon atoms, wherein (4) and/or (5) can be substituted with 1–3 fluorine, chlorine or bromine atoms, and (6) a cycloalkyl-methyl group with a total of 4–9 carbon atoms, $R^3$ is (1) hydrogen, (2) an alkyl group having 1–4 carbon atoms, (3) an alkenyl having 2–4 carbon atoms or (4) an alkynyl group having 2–4 carbon atoms, and further wherein $R^1$ and $R^3$ or $R^2$ and $R^3$ can form an alkylene bridge having 2–8 carbon atoms in which one $CH_2$ unit can be substituted by $NR^1$, an oxygen atom or a sulfur atom, Y is OH, $OR^4$ or 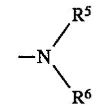 wherein, $R^4$ is an alkyl group having 1–4 carbon atoms, whose hydrogen atoms can be replaced entirely or partially by halogen atoms, $R^5$ is (1) hydrogen, (2) an alkyl group having 1–6 carbon atoms, (3) hydroxy- or (4) an alkoxy group having 1–6 carbon atoms, $R^6$ is (1) hydrogen, (2) an alkyl group having 1–6 carbon atoms, (3) a phenyl group or (4) a cycloalkyl group having 3–8 carbon atoms, and further wherein $R^5$ and $R^6$ can form a 5–6 membered ring with inclusion of the nitrogen atom, wherein said ring can contain an additional heteroatom.

2. A method of protecting plants as set forth in claim 1, wherein:

$R^1$ is (1) hydrogen or (2) an alkyl group having 1–3 carbon atoms, $R^2$ is (1) hydrogen, (2) an alkyl group having 1–6 carbon atoms, which can be substituted by an alkoxycarbonyl group having 1–6 carbon atoms, (3) a phenyl-, (4) an aralkyl having 7 or 8 carbon atoms or (5) a cycloalkyl group having 3–7 carbon atoms, $R^3$ is (1) hydrogen or (2) an alkyl group having 1–4 carbon atoms, $R^2$ and $R^3$ together form an alkylene bridge having 2 carbon atoms and Y is OH, $OR^4$ or $NR^5R^6$, wherein $R^4$ is an alkyl group having 1–4 carbon atoms, wherein the hydrogen atoms of said alkyl group can be entirely or partially replaced by fluorine atoms and $R^5$ and $R^6$ are each selected from the group consisting of (1) hydrogen (2) an alkyl having 1–4 carbon atoms, and (3) an alkoxy having 1–4 carbon atoms, and (4) $R^5$ and $R^6$ can form a 5–6 membered ring together with the nitrogen atom, wherein said ring can contain an additional nitrogen or oxygen atom.

3. A method of protecting plants as set forth in claim 1 or claim 2 in which Hal is bromine, n is the number 2 and $R^1$ is hydrogen.

4. A method of protecting plants as set forth in claim 1 or claim 2, wherein $R^2$ is (1) hydrogen or (2) an alkyl group having 1–4 carbon atoms, which can be unsubstituted or substituted by an alkoxy carbonyl group having 1–2 carbon atoms, $R^3$ is (1) hydrogen, (2) methyl or (3) ethyl and is OH, $OR^4$ or $NR^5R^6$ wherein $R^4$ is an alkyl group having 1–4 carbon atoms, and further wherein $R^5$ and $R^6$ are each selected from the group consisting of (1) hydrogen and (2) an alkyl group having 1–4 carbon atoms.

5. A method of protecting plants as set forth in claim 1 or claim 2 in which $Hal_n$ is 2 bromine atoms in positions 2' and 3' of the thiophene ring.

* * * * *